(12) United States Patent
Mou et al.

(10) Patent No.: US 10,737,022 B2
(45) Date of Patent: Aug. 11, 2020

(54) LIQUID SUPPLYING DEVICE FOR HUMAN INSULIN INJECTION

(71) Applicant: Microjet Technology Co., Ltd., Hsinchu (TW)

(72) Inventors: Hao-Jan Mou, Hsinchu (TW); Li-Pang Mo, Hsinchu (TW); Hsuan-Kai Chen, Hsinchu (TW); Chi-Feng Huang, Hsinchu (TW); Yung-Lung Han, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 198 days.

(21) Appl. No.: 16/149,565

(22) Filed: Oct. 2, 2018

(65) Prior Publication Data

US 2019/0125967 A1    May 2, 2019

(30) Foreign Application Priority Data

Oct. 27, 2017   (TW) .............................. 106137201 A

(51) Int. Cl.
*A61M 31/00* (2006.01)
*A61M 1/00* (2006.01)
(Continued)

(52) U.S. Cl.
CPC .... *A61M 5/16813* (2013.01); *A61M 5/14224* (2013.01); *A61M 5/14248* (2013.01);
(Continued)

(58) Field of Classification Search
None
See application file for complete search history.

(56) References Cited

U.S. PATENT DOCUMENTS 6,132,755 A * 10/2000 Eicher ................. A61M 31/002
424/427
6,558,361 B1   5/2003 Yeshurun
(Continued)

FOREIGN PATENT DOCUMENTS

CN         1190904 A      8/1998

OTHER PUBLICATIONS

Extended European Search Report, dated Dec. 18, 2018, for Application No. 16799928.3.

*Primary Examiner* — Rebecca E Eisenberg
(74) *Attorney, Agent, or Firm* — Birch, Stewart, Kolasch & Birch, LLP

(57) ABSTRACT

A liquid supplying device for a human insulin injection includes a substrate, a liquid storage chamber, a flow-guiding-and-actuating unit, a sensor and a driving chip. The flow-guiding-and-actuating unit includes a liquid guiding channel having a liquid guiding outlet in fluid communication with a liquid storage outlet of the liquid storage chamber. The sensor contacts with the human skin to measure a blood glucose level contained in sweat. The driving chip is configured to control the actuation of the flow-guiding-and-actuating unit, control open/closed states of the switching valves and receive the measured data from the sensor for determination. By driving the flow-guiding-and-actuating unit, a pressure gradient is generated, and an insulin liquid stored in the liquid storage chamber is transported to the liquid guiding outlet through the liquid guiding channel, flowing into a microneedle patch, and injected into a subcutaneous tissue through a plurality of hollow microneedles.

19 Claims, 7 Drawing Sheets

(51) Int. Cl.

| | |
|---|---|
| *A61M 5/168* | (2006.01) |
| *A61M 37/00* | (2006.01) |
| *A61M 5/142* | (2006.01) |
| *A61M 39/22* | (2006.01) |
| *A61M 5/172* | (2006.01) |
| *A61M 39/26* | (2006.01) |
| *A61M 5/145* | (2006.01) |
| *A61B 5/00* | (2006.01) |

(52) U.S. Cl.
CPC .... *A61M 5/14593* (2013.01); *A61M 5/16881* (2013.01); *A61M 5/1723* (2013.01); *A61M 37/0015* (2013.01); *A61M 39/223* (2013.01); *A61M 39/26* (2013.01); *A61B 5/4266* (2013.01); *A61M 2005/1726* (2013.01); *A61M 2037/003* (2013.01); *A61M 2037/0023* (2013.01); *A61M 2039/224* (2013.01); *A61M 2039/265* (2013.01); *A61M 2205/0244* (2013.01); *A61M 2205/0288* (2013.01); *A61M 2205/0294* (2013.01); *A61M 2205/3303* (2013.01); *A61M 2205/8206* (2013.01); *A61M 2230/201* (2013.01)

(56) References Cited

U.S. PATENT DOCUMENTS

| | | | |
|---|---|---|---|
| 6,623,457 B1 * | 9/2003 | Rosenberg | A61B 17/205 604/191 |
| 2002/0082543 A1 | 6/2002 | Park et al. | |
| 2004/0019331 A1 | 1/2004 | Yeshurun | |
| 2005/0137578 A1 | 6/2005 | Heruth et al. | |
| 2006/0255064 A1 | 11/2006 | Donaldson | |
| 2011/0142688 A1 * | 6/2011 | Chappel | F04B 43/043 417/213 |
| 2015/0057611 A1 * | 2/2015 | Bureau | A61M 37/0015 604/111 |
| 2017/0095184 A1 * | 4/2017 | Heikenfeld | A61B 5/0531 |
| 2019/0143090 A1 * | 5/2019 | Baker | A61M 37/0015 604/506 |
| 2019/0223795 A1 * | 7/2019 | Patolsky | A61B 5/14532 |

* cited by examiner

LIQUID SUPPLYING DEVICE FOR HUMAN INSULIN INJECTION

FIELD OF THE INVENTION

The present disclosure relates to a liquid supplying device, and more particularly to a liquid supplying device for a human insulin injection.

BACKGROUND OF THE INVENTION

In the current situation, the treatments of type 1 diabetes (Type 1 DM) and type 2 diabetes (Type 2 DM) are mainly to replenish hypoglycemic drugs, which are given by means of oral, syringe injection and insulin pump injection. As to the methods of oral and syringe injection, patients need to use their own blood glucose meter to detect their own blood glucose level, and then take the drug according to the blood glucose level. While in the insulin pump system, it consists of an indwelling needle and an insulin pump. The indwelling needle is placed in the body and fixed on the body surface for blood collection and drug injection. The insulin pump connected to the indwelling needle controls the release of the hypoglycemic drugs according to the blood glucose level.

Since insulin cannot be taken orally directly, only the injection methods can be used. However, injection through the syringe or the indwelling needle of the insulin pump not only causes pain to the patients during injection, but also leaves pinholes on the body surface. More specially, the syringe injection has to be operated multiple times a day, and it will cause subcutaneous tissue to produce lumps due to frequent injections. The use of the insulin pump with the indwelling needle reduces the number of injections, but the entire assembly has a certain volumetric weight, which is inconvenient to carry around, and the setting on the body will affect the patients' daily life and exercise.

Therefore, there is a need of providing a safe, portable, painless and intelligent liquid supplying device for the human insulin injection to address the above-mentioned issues in prior arts. It should be available for the patients to inject human insulin in daily life to control the blood glucose level at any time and solves the problems of the above conventional injection methods.

SUMMARY OF THE INVENTION

The object of the present disclosure is to provide a liquid supplying device for a human insulin injection. In order to solve the problem of that the conventional insulin injection method will cause pain and inconvenience to the patients, it provides a safe, portable, painless and intelligent liquid supplying device for the human insulin injection. It allows the patients to inject human insulin in daily life to control the blood glucose level at any time and serves as an artificial pancreas that automatically replenishes human insulin.

In accordance with an aspect of the present disclosure, a liquid supplying device for a human insulin injection is disclosed. The liquid supplying device includes a substrate, a liquid storage chamber, a flow-guiding-and-actuating unit, a plurality of switching valves, a microneedle patch, a sensor and a driving chip. The liquid storage chamber is disposed on the substrate and configured to store an insulin liquid, and has a liquid storage outlet. The flow-guiding-and-actuating unit is disposed on the substrate and has a liquid guiding channel in fluid communication with the liquid storage outlet. The liquid guiding channel has a liquid guiding outlet in fluid communication with the liquid storage outlet. The flow-guiding-and-actuating unit is enabled to transport and output the insulin liquid through the liquid guiding outlet. The plurality of switching valves has a first switching valve covering the liquid storage outlet and a second switching valve covering the liquid guiding outlet, respectively. The microneedle patch is attached under the flow-guiding-and-actuating unit and in communication with the liquid guiding outlet. The insulin liquid is transported into the microneedle patch through the liquid guiding outlet, and the microneedle patch has a plurality of hollow microneedles configured to be inserted into skin of a human subject with minimal invasion to introduce the insulin liquid into subcutaneous tissue of the human subject. The sensor is disposed on the substrate and configured to be in contact with the skin of the human subject to measure a blood glucose level contained in sweat and generate measured data. The driving chip is disposed on the substrate and configured to control the actuation of the flow-guiding-and-actuating unit, control open/closed states of the plurality of switching valves and receive the measured data from the sensor for determination. When the plurality of hollow microneedles of the microneedle patch are inserted into the skin of the human subject with minimal invasion and the sensor detects that the measured data of sweat meets a specific blood glucose level, the driving chip controls the actuation of the flow-guiding-and-actuation unit, controls the first switching valve in the liquid storage outlet to be in open state and controls the second switching valve in the liquid guiding outlet to be in open state. The insulin liquid within the liquid storage chamber is discharged through the liquid guiding outlet and flows into the microneedle patch. At last, the insulin liquid is discharged through the plurality of hollow microneedles and injected into the subcutaneous tissue of the human subject.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It should be noted that the following descriptions of preferred embodiments of this disclosure are presented herein for purpose of illustration and description only. It is not intended to be exhaustive or to be limited to the precise form disclosed.

Figure 1:
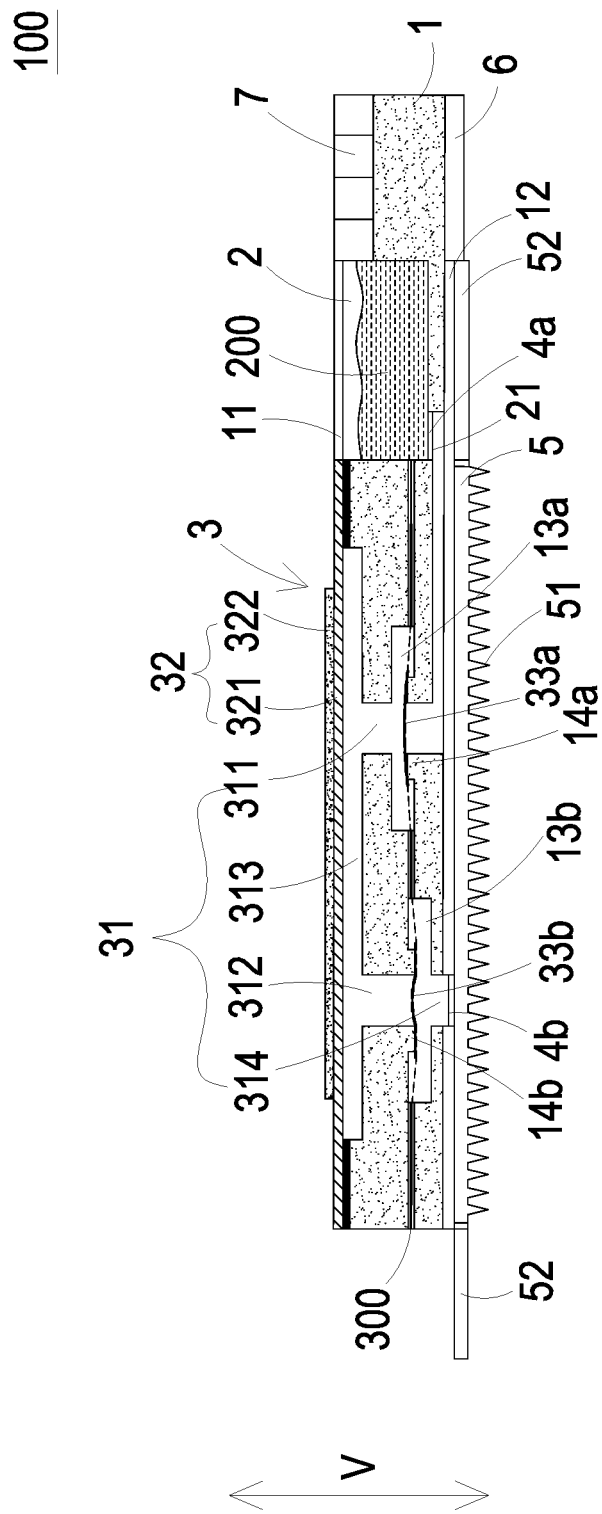
FIG. 1 is a cross sectional view illustrating a liquid supplying device for a human insulin injection according to an embodiment of the present disclosure.

Referring to FIG. 1, the present disclosure provides a liquid supplying device for the human insulin injection including at least one substrate 1, at least one liquid storage chamber 2, at least one insulin liquid 200, at least one liquid storage outlet 21, at least one flow-guiding-and-actuating unit 3, at least one liquid guiding channel 31, at least one liquid guiding outlet 314, a plurality of switching valves 4a, 4b, at least one microneedle patch 5, at least one sensor 6, at least one measured data, at least one driving chip 7 and at least one specific blood glucose level. The numbers of the substrate 1, the liquid storage chamber 2, the insulin liquid 200, the liquid storage outlet 21, the flow-guiding-and-actuating unit 3, the liquid guiding channel 31, the liquid guiding outlet 314, the microneedle patch 5, the sensor 6, the measured data, the driving chip 7 and the specific blood glucose level are exemplified by one for each respectively in the following embodiments but not limited thereto. It is noted that each of the substrate 1, the liquid storage chamber 2, the insulin liquid 200, the liquid storage outlet 21, the flow-guiding-and-actuating unit 3, the liquid guiding channel 31, the liquid guiding outlet 314, the microneedle patch 5, the sensor 6, the measured data, the driving chip 7 and the specific blood glucose level can also be provided in plural numbers.

Please refer to FIG. 1, which is a cross sectional view illustrating a liquid supplying device for a human insulin injection according to an embodiment of the present disclosure. The liquid supplying device 100 includes a substrate 1, a liquid storage chamber 2, a flow-guiding-and-actuating unit 3, a plurality of switching valves 4a and 4b, a microneedle patch 5, a sensor 6 and a driving chip 7. The liquid storage chamber 2, the flow-guiding-and-actuating unit 3, the plurality of switching valves 4a and 4b, the microneedle patch 5, the sensor 6 and the driving chip 7 are disposed on the substrate 1. The substrate 1 can be for example but not limited to a silicon chip or a printed circuit board (PCB). The sensor 6 and the driving chip 7 are integrated on the substrate 1 by a micro-electro-mechanical-system (MEMS) process. The liquid storage chamber 2 is concavely formed on the substrate 1 for accommodating the insulin liquid 200 and has a liquid storage outlet 21. The liquid storage chamber 2 concavely formed on the substrate 1 is covered by a cover 11.

In the embodiment, the flow-guiding-and-actuating unit 3 includes a liquid guiding channel 31 and an actuator 32. The structure of the liquid guiding channel 31 is formed within the interior of the substrate 1 and has an inlet channel 311, a compressing chamber 313, an outlet channel 312 and a liquid guiding outlet 314. The liquid guiding channel 31 is a fluid passage in communication between the liquid storage outlet 21 and the liquid guiding outlet 314. More specifically, the inlet channel 311 and the outlet channel 312 disposed on the substrate 1 are separated from each other and in communication with each other. The compressing chamber 313 concavely formed on the substrate 1 is in communication with first ends of the inlet channel 311 and the outlet channel 312, respectively. The top of the compressing chamber 313 is covered and sealed by the actuator 32. A second end of the inlet channel 311 in communication with the compressing chamber 313 is covered by a cover 12, so that a sealed fluid channel is formed at the second end of the inlet channel 311 in communication with the liquid storage outlet 21 of the liquid storage chamber 2, and an aperture (i.e., the liquid guiding outlet 314) is formed at a second end of the outlet channel 312 in communication with the compressing chamber 313. The liquid guiding channel 31 of the flow-guiding-and-actuating unit 3 is a fluid channel formed by sequentially connecting and communicating the inlet channel 311, the compressing chamber 313, the outlet channel 312 and the flow guiding outlet 314, which are described as the above.

In the embodiment, the actuator 32 includes a carrying member 321 and an actuating element 322. The carrying member 321 is a flexible board, which covers the compressing chamber 313 and fixed on the substrate 1. The actuating element 322 is a plate piezoelectric element, which is attached to a top surface of the carrying member 321. In response to an applied voltage, the actuating element 322 is deformed so as to drive the carrying member 321 to vibrate in a vertical direction (V) in a reciprocating manner. Thus, the volume of the compressing chamber 313 is increased or decreased to form a pressure gradient and thus the insulin liquid 200 stored in the liquid storage chamber 2 is transported to the inlet channel 311 and the outlet channel 312 and flows therethrough.

In the embodiment, the switching valve 4a and the switching valve 4b are disposed to cover the liquid storage outlet 21 and the liquid guiding outlet 314, respectively. The open and closed states of the switching valve 4a and the switching valve 4b are under control of the driving chip 7. Please refer to FIGS. 2A and 2B, which are schematic diagrams illustrating the actuations of switching valves according to an embodiment of the present disclosure. When the driving chip 7 controls the flow-guiding-and-actuating unit 3 to be actuated, the switching valve 4a and the switching valve 4b are in the open states. When the driving chip 7 controls the flow-guiding-and-actuating unit 3 to be disabled, the switching valve 4a and the switching valve 4b are in the closed states. The switching valve 4a and the switching valve 4b have identical structures. In order to avoid repeating the descriptions of the identical structures, the switching valve 4a is exemplified and described as follows merely. The switching valve 4a includes a sealing component 41, a stationary component 42 and a displacement component 43. The sealing component 41 has a plurality of first orifices 411. The stationary component 42 has a plurality of second orifices 421. The displacement component 43 is disposed within an accommodation space formed between the sealing component 41 and the stationary component 42, and has a plurality of third orifices 431. The plurality of third orifices 431 of the displacement component 43 are respectively corresponding in position to the plurality of second orifices 421 of the stationary component 42. That is, the plurality of third orifices 431 of the displacement component 43 are aligned with the plurality of second orifices 421 of the stationary component 42. The plurality of third orifices 431 of the displacement component 43 are misaligned with the plurality of first orifices 411 of the sealing component 41.

Figure 2A:
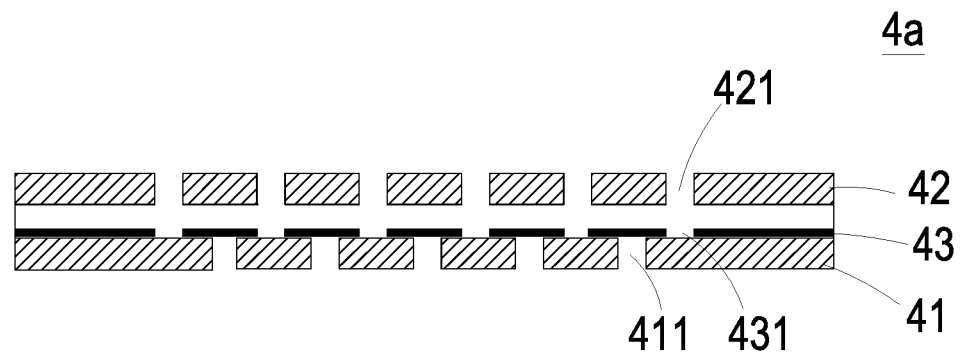
FIGS. 2A and 2B are schematic diagrams illustrating the actuations of switching valves according to an embodiment of the present disclosure.
Figure 2B:
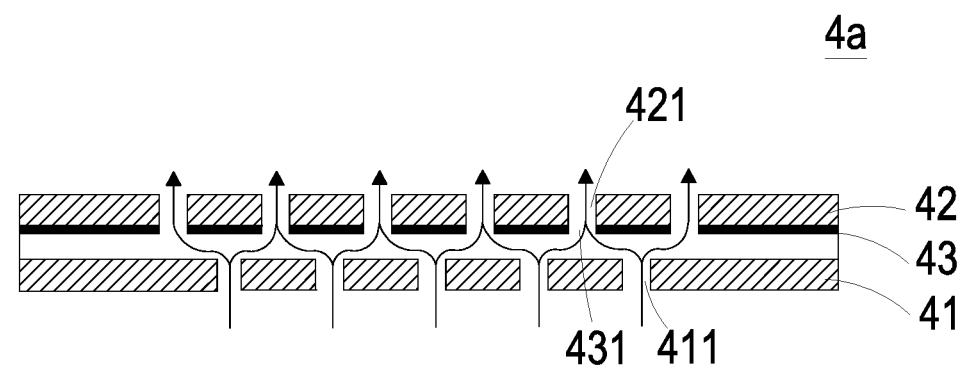

In a first aspect of the switching valve 4a in the present disclosure, the displacement component 43 is made of a charged material, and the stationary component 42 is made of a bipolar conductive material. In a second aspect of the switching valve 4a in the present disclosure, the displacement component 43 is made of a magnetic material, and the stationary component 42 is made of an electromagnet material and can be controlled to change its magnetic polarity. As shown in FIG. 2A, when the driving chip 7 controls the stationary component 42 and the displacement component 43 to be maintained in the same polarity, the displacement component 43 moves toward the sealing component 41 to close the switching valve 4a. As shown in FIG. 2B, when the driving chip 7 controls the stationary component 42 and the displacement component 43 to be maintained in opposite polarity, the displacement component 43 moves toward the stationary component 42 to open the switching valve 4a.

In the embodiment, the microneedle patch 5 has a plurality of hollow microneedles 51 and a patch area 52. The patch area 52 is a sticky thin slice. The microneedle patch 5 can be attached on the cover 12 disposed on the substrate 1 by utilizing the stickiness of the patch area 52, so that the entire microneedle patch 5 is fixed on the substrate 1 and on the side where the liquid guiding outlet 314 is exposed. The microneedle patch 5 can be attached on user's skin by utilizing another side of the patch area 52, so that the entire liquid supplying device 100 is positioned on the user's skin without falling. The plurality of hollow microneedles 51 of the microneedle patch 5 are micron-sized needles capable of puncturing the patient's skin. The hollow microneedles 51 may be made of a material such as a high molecular polymer, a metal or silicon. Preferably but not exclusively, the hollow microneedles 51 are made of silicon dioxide with high biocompatibility. The hollow microneedles 51 have specific diameters for allowing the insulin molecules to pass through. Preferably, the hollow microneedle 51 has an internal diameter ranging from 10 μm to 550 μm. The hollow microneedle 51 has a length ranging from 400 μm to 900 μm. The hollow microneedles 51 can puncture into human's subcutaneous tissue till a depth and without contacting any nerve. Therefore, the puncture of the hollow microneedles 51 is painless. The hollow microneedles 51 are disposed on the microneedle patch 5 and arranged in array. The plurality of hollow microneedles 51 are spaced from each other a distance greater than 200 μm so that the injection flow from the hollow microneedles 51 may not interfere with each other. Under circumstances when blockage of one or more hollow microneedles 51 occurs, the arrangement of the hollow microneedles 51 in the array can prevent the flow injection function from being impacted and allow the rest of the hollow microneedles 51 to maintain the flow injection function continuously.

Figure 3:
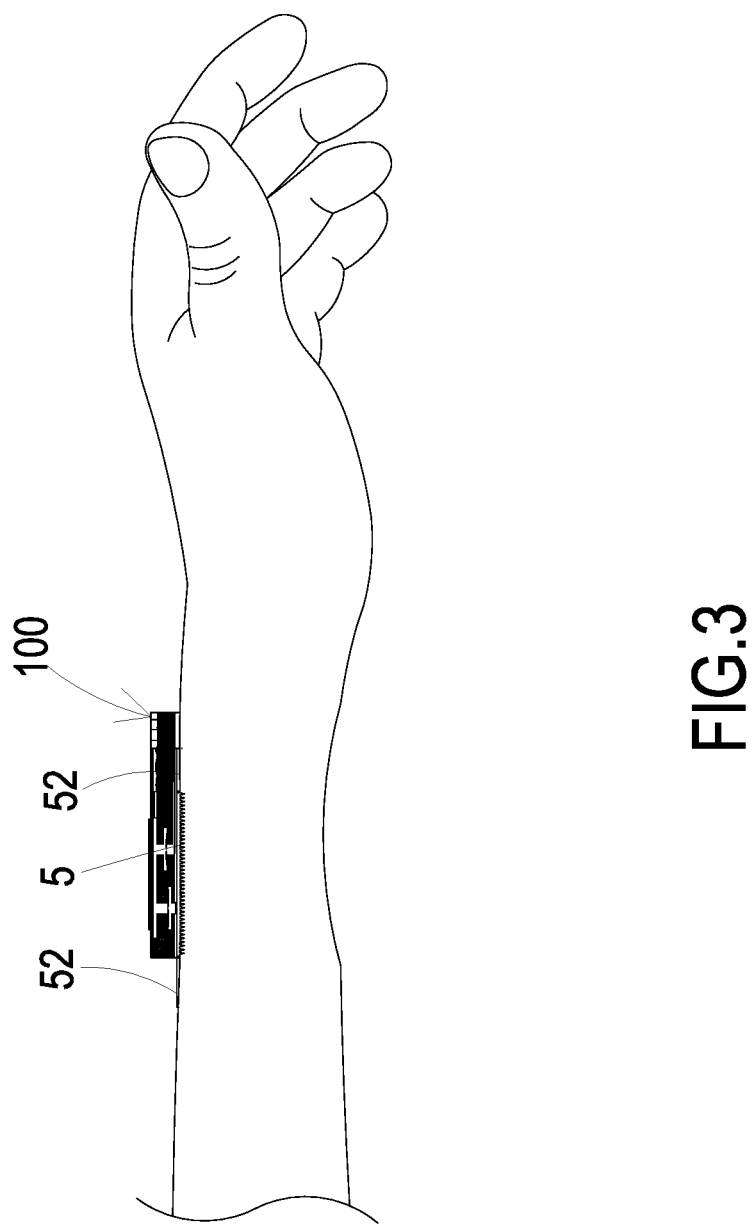
FIG. 3 is a schematic diagram illustrating the liquid supplying device for the human insulin injection to be worn on user's body.

Please refer to FIG. 3, which is a schematic diagram illustrating the liquid supplying device for the human insulin injection to be worn on user's body. As shown in the drawing, the liquid supplying device 100 is in a thin plate shape and has a miniature size. Combining with the patch area 52 of the microneedle patch 5, the liquid supplying device 100 can be attached and fixed on the human's skin. Thus, the liquid supplying device 100 can be positioned on any position of the human body by utilizing the stickiness of the patch area 52 merely.

Figure 4:
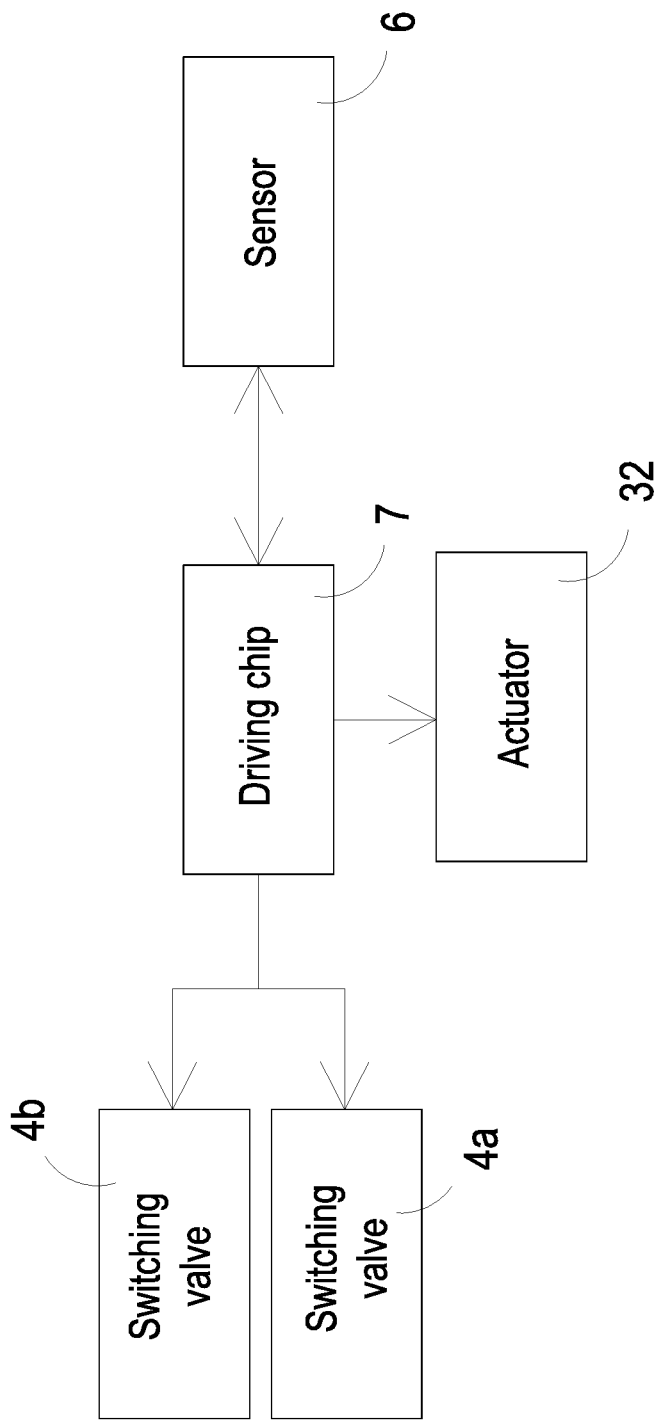
FIG. 4 is a circuit block diagram of the liquid supplying device for the human insulin injection according to an embodiment of the present disclosure.

Please refer to FIGS. 1 and 4. FIG. 4 is a circuit block diagram of the liquid supplying device for the human insulin injection according to an embodiment of the present disclosure. The sensor 6 is integrated via the micro-electro-mechanical-system (MEMS) procedure and mounted on the substrate 1. When the liquid supplying device 100 is positioned on the user's skin, the sensor 6 contacts with the user's skin for monitoring the blood glucose level contained in the sweat so that the blood glucose level can be acquired and measured data corresponding to the blood glucose level is generated. The driving chip 7 is integrated via the micro-electro-mechanical-system (MEMS) procedure and mounted on the substrate 1. The driving chip 7 is electrically connected to the actuator 32 of the flow-guiding-and-actuating unit 3, the switching valves 4a, 4b and the sensor 6. Thus, the driving chip 7 can transmit a control signal to control the actions of the actuator 32 of the flow-guiding-and-actuating unit 3, control the open/closed states of the switching valve 4a and the switching valve 4b and receive the measured data from the sensor 6 for determination. Preferably but not exclusively, the driving chip 7 includes a graphene battery to supply power.

Figure 5A:
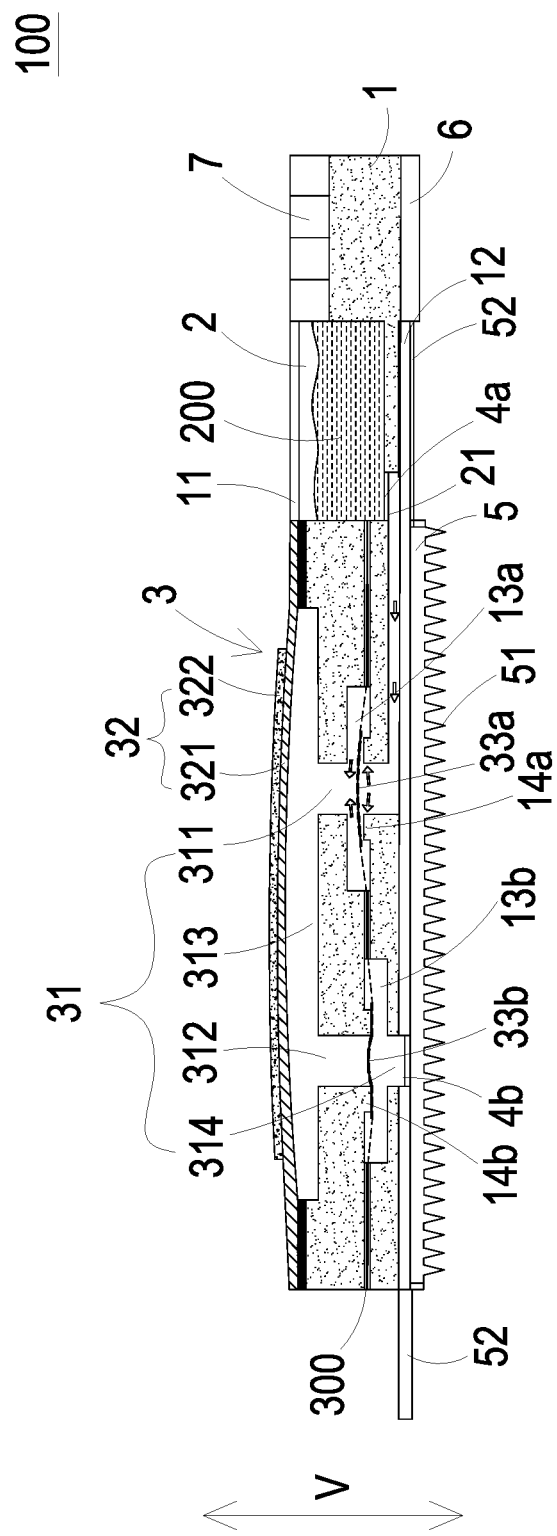
FIGS. 5A and 5B are schematic diagrams illustrating actions of the liquid supplying device for the human insulin injection according to an embodiment of the present disclosure.
Figure 5B:
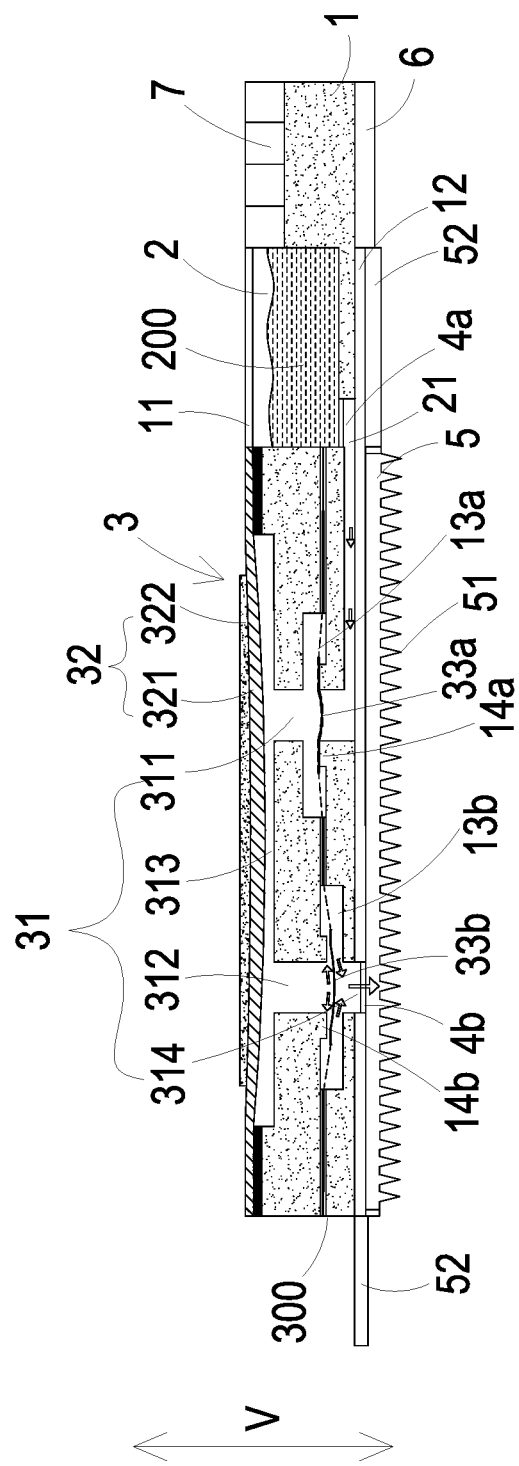

Please refer to FIGS. 5A and 5B, which are schematic diagrams illustrating actions of the liquid supplying device for the human insulin injection according to an embodiment of the present disclosure. When the sensor 6 detects that the measured data meets a specific blood glucose level, the driving chip 7 transmits a start signal to the flow-guiding-and-actuating unit 3 to actuate the actuator 32 and control the switching valve 4a and the switching valve 4b to be in the open state. When the actuating element 322 is actuated to generate deformation caused by reverse piezoelectric effect in response to an applied voltage, the carrying member 321 is driven to move in resonance. At this time, the actuator 32 is driven to vibrate in a vertical direction (V) in a reciprocating manner. As shown in FIG. 5A, when the actuator 32 is actuated to deform and vibrate upwardly, the volume of the compressing chamber 313 is enlarged to result in suction. In response to the suction, the insulin liquid 200 is outputted through the liquid storage outlet 21 and transported into the compressing chamber 313. Then, as shown in FIG. 5B, when the actuator 32 is driven to deform and vibrate downwardly, the volume of the compressing chamber 313 is shrunken to result in a pushing force. In response to the pushing force, the volume of the compressing chamber 313 is compressed and the insulin liquid 200 converged in the compressing chamber 313 is compressed and transported downwardly to the liquid guiding outlet 314 through the outlet channel 312, and thus transported to the plurality of hollow microneedles 51 of the microneedle patch 5. Then, a certain amount of the insulin liquid 200 is injected into the subcutaneous tissue of the human body. Certainly, if it is necessary to refill the insulin liquid 200 to meet the required amount, the above-mentioned actuating device 32 is repeatedly operated to vibrate in a vertical direction (V) in a reciprocating manner continuously. Again, the insulin liquid 200 is transported from the liquid storage outlet 21 through the liquid guiding channel 31 to the liquid guiding outlet 314 and then injected into the human subcutaneous tissue through the plurality of hollow microneedles 51. The liquid supplying device 100 can be used as an artificial pancreas to replenish the human insulin automatically.

Figure 6:
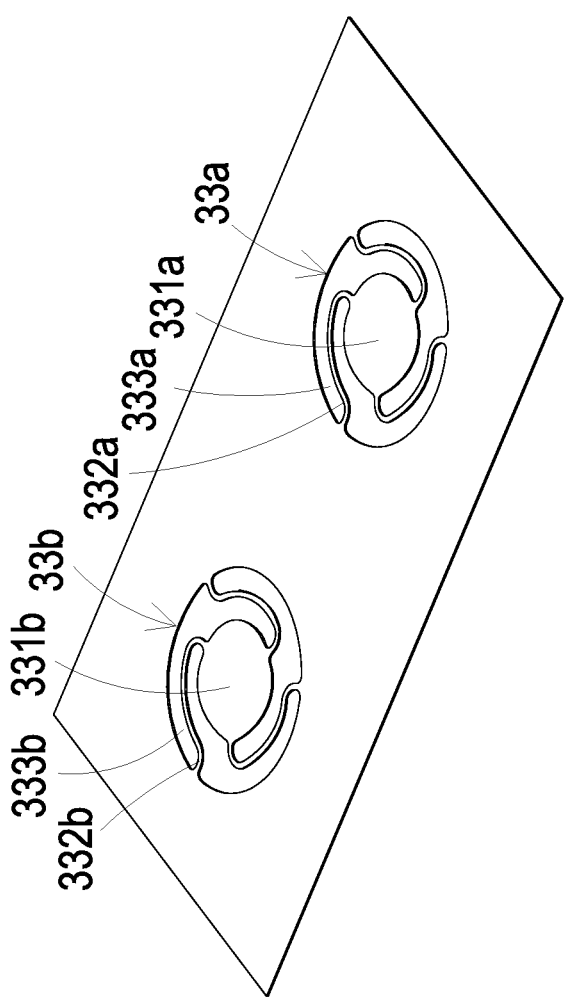
FIG. 6 is a schematic structural view illustrating the valve membrane according to an embodiment of the present disclosure.

In the embodiment, as shown in FIG. 1, the liquid supplying device 100 further includes a valve membrane 300 disposed in both of the inlet channel 311 and the outlet channel 312 of the substrate 1 to avoid backflow of the transporting liquid. Please refer to FIGS. 1 and 6. FIG. 6 is a schematic structural view illustrating the valve membrane according to an embodiment of the present disclosure. More specifically, the substrate 1 further includes a first chamber 13a located at a middle area of the inlet channel 311 and a second chamber 13b located at a middle area of the outlet channel 312. The valve membrane 300 is embedded within the substrate 1 to cover the inlet channel 311 and the outlet channel 312. As shown in FIG. 6, the valve membrane 300 is made by a flexible membrane. The valve membrane 300 includes a first valve plate 33a spatially corresponding to and covering the inlet channel 311 and a second valve plate 33b spatially corresponding to and covering the outlet channel 312. The first valve plate 33a includes a central part 331a and a plurality of connection parts 332a connected to the central part 331a, so that the central part 331a can be elastically supported by the connection parts 332a on the valve membrane 300. The first valve plate 33a further includes a plurality of hollow parts 333a arranged among the plurality of connection parts 332a for allowing the fluid to flow therethrough. Namely, the first valve plate 33a is formed by the central part 331a, the connection parts 332a and the hollow parts 333a described as the above. Similarly, the second valve plate 33b is formed by the central part 331b, the connection parts 332b and the hollow parts 333b to construct the same structure as the first valve plate 33a.

Please refer to FIG. 1 again. The substrate 1 further has a first convex structure 14a disposed within the inlet channel 311 and a second convex structure 14b disposed within the outlet channel 312. The first convex structure 14a is in position corresponding to the inlet channel 311 and disposed on the bottom of the first chamber 13a. The second convex structure 14b is in position corresponding to the outlet channel 312 and disposed on the top of the second chamber 13b. Installation of each convex structure can provide a pre-force that makes the first convex structure 14a be in close contact with the central part 331a of the first valve plate 33a and the second convex structure 14b be in close contact with the central part 331b of the second valve 33b. With the above arrangement, when the actuator 32 is in a non-enabled state, the first valve plate 33a seals and blocks the inlet channel 311 and the second valve plate 33b seals and blocks the outlet channel 312, the backflow of the insulin liquid 200 transported between the inlet channel 311 and the outlet channel 312 can be avoided.

In more detail, when the actuator 32 is actuated to deform and vibrate upwardly, the volume of the compressing chamber 313 is enlarged to result in the suction. The first valve plate 33a within the inlet channel 311 is driven to move upwardly in response to the suction. Consequently, the central part 331a of the first valve plate 33a moves away from the first convex structure 14a rapidly and the inlet channel 311 is opened. Under this circumstance, the insulin liquid 200 can flow into the compressing chamber 313 through the plurality of hollow parts 333a and the first chamber 13a. When the actuator 32 is actuated to deform and vibrate downwardly, the volume of the compressing chamber 313 is compressed to result in the pushing force. The second valve plate 33b within the outlet channel 312 is driven to move downwardly in response to the pushing force. Consequently, the central part 331b of the second valve plate 33b moves away from the second convex structure 14b rapidly and the outlet channel 312 is opened. Under this circumstance, the insulin liquid 200 in the liquid guiding channel 31 can flow into the second chamber 13b through the plurality of hollow parts 333b, be transported to the liquid guiding outlet 314 through the outlet channel 312 and then transported to the plurality of hollow microneedles 51 of the microneedle patch 5. Then, a certain amount of the insulin liquid 200 is injected into the subcutaneous tissue of the human body. Meanwhile, the first valve plate 33a within the inlet channel 311 is subjected to the volume change of the compressing chamber 313 to generate a pushing force, thereby causing the central part 331a of the first valve plate 33a to return to the state made by the pre-force that the first convex structure 14a abuts against the first valve plate 33a (see FIG. 5B). Thus, the inlet channel 311 is sealed and the insulin liquid 200 won't flow backward through the inlet channel 311.

The present disclosure relates a safe, portable, painless and intelligent liquid supplying device 100 for the human insulin injection. The liquid supplying device 100 is provided for the patients to inject the human insulin in daily life so as to control the blood glucose level with accuracy at any time. Although it is a miniaturized device and the unit quantity of the insulin liquid 200 stored in the liquid storage chamber 2 is limited, the insulin liquid 200 can also be introduced into the liquid storage chamber 2 through the pipeline connected externally. Thus, a portable container for replenishing the human insulin is connected to and communicated with the liquid storage chamber 2 to form a continuous liquid supply mode.

In summary, the present disclosure provides the liquid supplying device 100. When the sensor 6 of the liquid supplying device 100 detects that the blood glucose level of the patient is too high, the actuator 32 of the flow-guiding-and-actuating unit 3 is driven to change the volume of the compressing chamber 313. Thus, the pressure gradient is generated to make the insulin liquid 200 stored in the liquid storage chamber 2 flow out. The insulin liquid 200 is transported to the microneedle patch 5 attached under the flow-guiding-and actuating unit 3 through the liquid guiding channel 31, and automatically injected into the subcutaneous tissue through the plurality of hollow microneedles 51 of the microneedle patch 5. It serves as an artificial pancreas to automatically replenish the human insulin. In addition, with the setting of the switching valve 4a and the switching valve 4b, the injection volume of the insulin liquid 200 can be accurately controlled and the backflow is avoided. Comparing to the conventional insulin injection method, the liquid supplying device 100 of the present disclosure has the advantages of painless operation, portable structure and automatic detection of injection timing. It is highly industrially utilized, so as to file a patent application.

While the disclosure has been described in terms of what is presently considered to be the most practical and preferred embodiments, it is to be understood that the disclosure needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A liquid supplying device for a human insulin injection, comprising:
   a substrate;
   a liquid storage chamber disposed on the substrate, configured to store an insulin liquid, and having a liquid storage outlet;
   a flow-guiding-and-actuating unit disposed on the substrate and having a liquid guiding channel in fluid communication with the liquid storage outlet, wherein the liquid guiding channel has a liquid guiding outlet in fluid communication with the liquid storage outlet, wherein the flow-guiding-and-actuating unit is enabled to transport the insulin liquid and then discharge the insulin liquid through the liquid guiding outlet;
   a plurality of switching valves having a first switching valve covering the liquid storage outlet and a second switching valve covering the liquid guiding outlet, respectively;
   a microneedle patch attached under the flow-guiding-and-actuating unit and in communication with the liquid guiding outlet, wherein the insulin liquid is transported into the microneedle patch through the liquid guiding outlet, and the microneedle patch has a plurality of hollow microneedles configured to be inserted into skin of a human subject with minimal invasion to introduce the insulin liquid into subcutaneous tissue of the human subject;

a sensor disposed on the substrate and configured to be in contact with the skin of the human subject to measure a blood glucose level contained in sweat and generate measured data correspondingly; and a driving chip disposed on the substrate and configured to control the actuation of the flow-guiding-and-actuating unit, control open/closed states of the plurality of switching valves and receive the measured data from the sensor for determination;

wherein when the plurality of hollow microneedles of the microneedle patch are inserted into the skin of the human subject with minimal invasion and the sensor detects that the measured data of sweat meets a specific blood glucose level, the driving chip controls the actuation of the flow-guiding-and-actuation unit, controls the first switching valve in the liquid storage outlet to be in open state and controls the second switching valve in the liquid guiding outlet to be in open state so that the insulin liquid within the liquid storage chamber is discharged through the liquid guiding outlet and flows into the microneedle patch, whereby the insulin liquid is further discharged through the plurality of hollow microneedles and injected into the subcutaneous tissue of the human subject.

2. The liquid supplying device for the human insulin injection according to claim 1, wherein the liquid guiding channel of the flow-guiding-and-actuating unit is disposed within the substrate and comprises an inlet channel, a compressing chamber, an outlet channel and the liquid guiding outlet, wherein the inlet channel is in fluid communication with the liquid storage outlet of the liquid storage chamber, wherein the outlet channel is in fluid communication with the flow guiding outlet, wherein the inlet channel and the outlet channel are separated from each other and are in fluid communication with each other through the compressing chamber, wherein the flow-guiding-and-actuating unit has an actuator covering and sealing the compressing chamber, and the actuator is used to compress the volume of the compressing chamber so as to form a pressure gradient between the inlet channel and the outlet channel, thereby allowing and pushing the insulin liquid to flow.

3. The liquid supplying device for the human insulin injection according to claim 2, wherein the actuator comprises a carrying member and an actuating element, wherein the carrying member covers and seals the compressing chamber, and the actuating element is attached to a surface of the carrying member, wherein the actuating element is subject to deformation that drives the carrying member to deform in resonance so as to compress the volume of the compressing chamber to form the pressure gradient between the inlet channel and the outlet channel, thereby allowing and pushing the insulin liquid to flow.

4. The liquid supplying device for the human insulin injection according to claim 1, wherein the actuating element is a piezoelectric component.

5. The liquid supplying device for the human insulin injection according to claim 2, further comprising a valve membrane and a plurality of convex structures, wherein the valve membrane is disposed in the inlet channel and the outlet channel and the plurality of convex structures are disposed in the inlet channel and the outlet channel respectively, wherein each convex structure is disposed to provide a pre-force that abuts against the valve membrane, so as to control the inlet channel and the outlet channel to be in an open state or a closed state for preventing the insulin liquid from flowing backward.

6. The liquid supplying device for the human insulin injection according to claim 1, wherein the driving chip comprises a graphene battery for providing power.

7. The liquid supplying device for the human insulin injection according to claim 1, wherein the switching valve comprises a sealing component, a stationary component and a displacement component, wherein the displacement component is disposed between the stationary component and the sealing component, the sealing component has a plurality of first orifices, the stationary component has a plurality of second orifices, and the displacement component has a plurality of third orifices, wherein the plurality of third orifices of the displacement component are aligned with the plurality of second orifices of the stationary component, and the plurality of second orifices of the stationary component are misaligned with the plurality of first orifices of the sealing component.

8. The liquid supplying device for the human insulin injection according to claim 7, wherein the displacement component is made of a charged material, and the stationary component is made of a bipolar conductive material, wherein the displacement component and the stationary component are maintained in opposite polarity, and the displacement component moves toward the stationary component so that the switching valve is in the open state.

9. The liquid supplying device for the human insulin injection according to claim 8, wherein the polarity of the stationary component is controlled by the driving chip.

10. The liquid supplying device for the human insulin injection according to claim 7, wherein the displacement component is made of a charged material, and the stationary component is made of a bipolar conductive material, wherein the displacement component and the stationary component are maintained in the same polarity, and the displacement component moves toward the sealing component so that the switching valve is in the closed state.

11. The liquid supplying device for the human insulin injection according to claim 10, wherein the polarity of the stationary component is controlled by the driving, chip.

12. The liquid supplying device for the human insulin injection according to claim 7, wherein the displacement component is made of a magnetic material, and the stationary component is made of an electromagnet material whose magnetic polarity is changeable under control, wherein the displacement component and the stationary component are maintained in opposite polarity, and the displacement component moves toward the stationary component so that the switching valve is in the open state.

13. The liquid supplying device for the human insulin injection according to claim 12, wherein the polarity of the stationary component is controlled by the driving chip.

14. The liquid supplying device for the human insulin injection according to claim 7, wherein the displacement component is made of a magnetic material, and the stationary component is made of an electromagnet material whose magnetic polarity is changeable under control, wherein the displacement component and the stationary component are maintained in the same polarity, and the displacement component moves toward the sealing component so that the switching valve is in the closed state.

15. The liquid supplying device for the human insulin injection according to claim 14, wherein the polarity of the stationary component is controlled by the driving chip.

16. The liquid supplying device for the human insulin injection according to claim 1, wherein each of the plurality of hollow microneedles of the microneedle patch has an inner diameter ranging from 10 μm to 550 μm and a length ranging from 400 μm to 900 μm.

17. The liquid supplying device for the human insulin injection according to claim 1, wherein the plurality of hollow microneedles are arranged in an array, and the plurality of hollow microneedles are spaced from each other a distance greater than 200 μm.

18. The liquid supplying device for the human insulin injection according to claim 1, wherein the plurality of the hollow microneedles are made of silicon dioxide.

19. A liquid supplying device for the human insulin injection, comprising:

- at least one substrate;
- at least one liquid storage chamber disposed on the substrate, configured to store at least one insulin liquid, and having at least one liquid storage outlet;
- at least one flow-guiding-and-actuating unit disposed on the substrate and having at least one liquid guiding channel in fluid communication with the liquid storage outlet, wherein the liquid guiding channel has at least one liquid guiding outlet in fluid communication with the liquid storage outlet, wherein the flow-guiding-and-actuating unit is enabled to transport the insulin liquid and then discharge the insulin liquid through the liquid guiding outlet;
- a plurality of switching valves having a first switching valve covering the liquid storage outlet and a second switching valve covering the liquid guiding outlet, respectively;
- at least one microneedle patch attached under the flow-guiding-and-actuating unit and in communication with the liquid guiding outlet, wherein the insulin liquid is transported into the microneedle patch through the liquid guiding outlet, and the microneedle patch has a plurality of hollow microneedles configured to be inserted into skin of a human subject with minimal invasion to introduce the insulin liquid into subcutaneous tissue of the human subject;
- at least one sensor disposed on the substrate and configured to be in contact with the skin of the human subject to measure a blood glucose level contained in sweat and generate at least one measured data correspondingly; and
- at least one driving chip disposed on the substrate and configured to control the actuation of the flow-guiding-and-actuating unit, control open/closed states of the plurality of switching valves and receive the measured data from the sensor for determination;

wherein when the plurality of hollow microneedles of the microneedle patch are inserted into the skin of the human subject with minimal invasion and the sensor detects that the measured data of sweat meets at least one specific blood glucose level, the driving chip controls the actuation of the flow-guiding-and-actuation unit, controls the first switching valve in the liquid storage outlet to be in open state and controls the second switching valve in the liquid guiding outlet to be in open state so that the insulin liquid within the liquid storage chamber is discharged through the liquid guiding outlet and flows into the microneedle patch, whereby the insulin liquid is further discharged through the plurality of hollow microneedles and injected into the subcutaneous tissue of the human subject.

\* \* \* \* \*